(12) United States Patent
Konno

(10) Patent No.: US 6,537,208 B1
(45) Date of Patent: Mar. 25, 2003

(54) OPTICAL IMAGING SYSTEM WITH MOVABLE SOLID-STATE IMAGING DEVICE FOR FOCUS CONTROL

(75) Inventor: Mitsujiro Konno, Hino (JP)

(73) Assignee: Olympus Optical Co., Ltd., Tokyo (JP)

( * ) Notice: Subject to any disclaimer, the term of this patent is extended or adjusted under 35 U.S.C. 154(b) by 189 days.

(21) Appl. No.: 09/657,466

(22) Filed: Sep. 7, 2000

(30) Foreign Application Priority Data

Sep. 8, 1999 (JP) .......................... 11-254447

(51) Int. Cl.⁷ .................... A61B 1/05; H04N 5/225
(52) U.S. Cl. ........................ 600/167; 348/340
(58) Field of Search .................... 600/167, 168, 600/109, 130, 176; 359/363, 663; 348/340

(56) References Cited

U.S. PATENT DOCUMENTS

| | | | | |
|---|---|---|---|---|
| 4,598,980 A | * | 7/1986 | Doi et al. .................... | 359/735 |
| 5,050,974 A | * | 9/1991 | Takasugi et al. ............ | 359/663 |
| 5,175,650 A | * | 12/1992 | Takayama et al. ......... | 359/644 |
| 5,208,702 A | * | 5/1993 | Shiraiwa .................... | 359/663 |
| 5,633,754 A | * | 5/1997 | Hoogland .................. | 359/434 |
| 5,704,896 A | * | 1/1998 | Fukunishi et al. ......... | 348/340 |
| 5,777,797 A | * | 7/1998 | Miyano ...................... | 359/660 |
| 5,797,836 A | * | 8/1998 | Lucey et al. ................ | 600/109 |
| 6,117,071 A | * | 9/2000 | Ito et al. ..................... | 600/118 |
| 6,142,934 A | * | 11/2000 | Lagerway et al. .......... | 600/156 |
| 6,252,723 B1 | * | 6/2001 | Nagaoka .................... | 359/652 |

FOREIGN PATENT DOCUMENTS

| | | | |
|---|---|---|---|
| JP | 2-18513 A | * | 1/1990 |
| JP | 2-168216 A | * | 6/1990 |
| JP | 6-3495 | | 1/1994 |

* cited by examiner

Primary Examiner—John P. Leubecker
(74) Attorney, Agent, or Firm—Pillsbury Winthrop LLP

(57) ABSTRACT

An image pickup optical system for use in a magnifying endoscope or the like in which focus control is effected by moving a solid-state image pickup device. When a simultaneous solid-state image pickup device is used, color shading is suppressed satisfactorily, and flare-preventing measures are taken satisfactorily. Further, the center of the field and the center axis of the endoscope are allowed to coincide with each other at a reduced cost. The optical system is capable of being focused at a plurality of object distances by moving a solid-state image pickup device. The optical system is provided with a field lens by which light rays whose incident angle varies in accordance with focus control are made telecentric.

11 Claims, 8 Drawing Sheets

OPTICAL IMAGING SYSTEM WITH MOVABLE SOLID-STATE IMAGING DEVICE FOR FOCUS CONTROL

This application claims benefit of Japanese Application No. Hei 11-254447 filed in Japan on Sep. 8, 1999, the contents of which are incorporated by this reference.

BACKGROUND OF THE INVENTION

The present invention relates to an endoscope system and, more particularly, to an image pickup optical system of an endoscope system that uses a solid-state image pickup device.

Video endoscopes using a small-sized CCD (solid-state image pickup device) have been prevailing in recent years. This type of endoscopes allows a large number of people to observe the morbid part in the patient's body cavity on a monitor and hence permits the patient to be examined and diagnosed by a plurality of doctors. It is also possible for the patient to be diagnosed while observing his/her own morbid part. This is a great advantage. Among these endoscopes, so-called magnifying endoscopes have attracted special interest recently. The magnifying endoscopes allow close-up observation of the morbid part to inspect the micro-structure thereof, thereby deciding the degree of infiltration in a small morbid region and determining an extent to which the morbid part should be excised. This type of magnifying endoscope requires focus control to be effected according to the object distance differing for different observation modes, i.e. normal observation and close-up observation.

For example, Japanes Patent Post-Exam Publication Number (hereinafter referred to as "JP") Hei 6-3495 discloses a mechanical arrangement for moving a solid-state image pickup device without moving an optical system to effect focus control. The disclosed arrangement allows realization of an endoscope having a smaller amount of decentration of lenses than in the case of an arrangement in which focus control is effected by moving the optical system.

Meanwhile, simultaneous solid-state image pickup devices in which color filters are placed in front of light-receiving parts have been remarkably reduced in both size and cost: in recent years. Accordingly, the application of such a simultaneous solid-state image pickup device to an endoscopes is under consideration. FIG. 8 is a conceptual view of the cross-section of a simultaneous solid-state image pickup device. Light-receiving parts 1 are photodiodes for converting light into electric signals. A color filter 2 is placed in correspondence to each light-receiving part 1. Normally, a light beam 3 passes through a color filter 2 corresponding to each pixel, and an electric signal outputted from each light-receiving part 1 is computed in an electric signal processing circuit (not shown) to generate a color signal.

However, when there is a light beam 4 entering at a large incident angle, light passing through a color filter 2 corresponding to a light-receiving part 1 next to the light-receiving part 1 for the light beam 3 enters the latter light-receiving part 1. As a result, an unwanted electric signal is outputted correspondingly. If this signal is subjected to normal signal processing, color reproduction different from normal results undesirably. In the ordinary optical system, the incident angle increases as the image height increases. Therefore, the periphery of the image is undesirably colored owing to the above-described phenomenon. This problem is known as "color shading".

FIG. 9 is a conceptual view showing the image position 5' and the solid-state image pickup device position 5 when the optical system of JP Hei 6-3495 is focused on a far object and also showing the image position 6' and the solid-state image pickup device position 6 when the optical system is focused on a near object. In the figure, the angle at which a light ray 8 from the near object is incident on the solid-state image pickup device varies to a considerable extent with respect to a light ray 7 from the far object because of the change in position of the solid-state image pickup device. This gives rise to the problem of color shading phenomenon accompanying focus control when a simultaneous solid-state image pickup device is used. JP Hei 6-3495 is an invention relating to a method of simply moving a solid-state image pickup device and makes no mention of the problem of color shading phenomenon.

Endoscopes are wide-angle optical systems having a field angle ranging from 120° to 140°. Therefore, it is likely that rays outside the field angle will collect at a position near the effective image pickup area to produce flare. FIG. 10 is a diagram showing a light ray 9 at the maximum field angle in a wide-angle optical system, together with light 10 outside the field. Light 10 outside the field emanates from an object outside the field, e.g. a bright spot in a mucous membrane of high reflectance, and forms an image at a position extremely close to the image-formation position of the light ray 9 at the maximum field angle. If a structural member or portion of a solid-state image pickup device 11 is present at the image-formation position of the light 10, it serves as a secondary light source, and scattered light is generated therefrom and enters an effective area 13 as unwanted light 12. Therefore, it is necessary to place a flare stop 14 so as to prevent the light 10 from entering the solid-state image pickup device 11.

However, in the arrangement wherein the solid-state image pickup device moves, the incident angle of rays on the solid-state image pickup device varies, as shown in FIG. 9. Consequently, the ray height at the position of the flare stop 14 varies. Therefore, flare cannot satisfactorily be prevented because of focus control. JP Hei 6-3495 makes no mention of the problem how to prevent the occurrence of flare.

Further, in JP Hei 6-3495, the solid-state image pickup device is moved by using the outer periphery thereof as a guide. In general, however, there are variations in the displacement of the outer periphery of the solid-state image pickup device with respect to the center of the image pickup area. That is, the invention disclosed in JP Hei 6-3495 involves the problem that the center of the field is displaced from the center axis of the endoscope. If the solid-state image pickup device is arranged so that the center of the outer periphery of the image pickup device and the center of the image pickup area are made,coincident with each other in order to prevent the occurrence of the above-described problem, the solid-state image pickup device becomes costly.

SUMMARY OF THE INVENTION

In view of the above-described problems with the prior art, an object of the present invention is to provide an image pickup optical system for use in a magnifying endoscope or the like in which focus control is effected by moving a solid-state image pickup device, which is designed so that when a simultaneous solid-state image pickup device is used, color shading is suppressed satisfactorily, and flare-preventing measures are taken satisfactorily, and further the center of the field and the center axis of the endoscope are allowed to coincide with each other at a reduced cost.

According to a first aspect thereof, the present invention provides an image pickup optical system that is an optical system capable of being focused at a plurality of object distances by moving a solid-state image pickup device. The optical system includes an optical element by which light rays whose incident angle varies in accordance with focus control are made telecentric.

FIG. 1 is a conceptual view for describing the image pickup optical system according to the present invention. A pupil-varying field lens 15 is placed on the object side of a movable solid-state image pickup device 11 to make light rays entering the solid-state image pickup device 11 close to being telecentric. Consequently, a light ray 7 from a far object and a light ray 8 from a near object can be passed through a color filter corresponding to each light-receiving part.

Thus, it is possible to prevent color shading irrespective of the movement of the solid-state image pickup device.

Further; it is desirable for the present invention to satisfy the following condition:

$$\theta < \tan^{-1}(p/2L) \quad (1)$$

where θ is the maximum incident angle of rays, inclusive of the angle subtended by rays that depends on the F-number; p is the pixel pitch; and L is the distance to the farthest color filter from the light-receiving part.

Thus, it is possible to define the incident angle and the angle subtended by rays so that a light ray will not pass through a color filter corresponding to a neighboring pixel. The color shading gives rise to a problem particularly in a CCD of high pixel density. The reason for this is that it is necessary to reduce the angle of oblique incidence because the pixel pitch p in the condition (1) is small.

One of the objects of the present invention is to provide a magnifying endoscope, and the purpose of observing an enlarged image of the morbid part is to inspect the microstructure thereof. Therefore, increasing the number of pixels of the solid-state image pickup device is very effective. Accordingly, the present invention is particularly effective when combined with a solid-state image pickup device of high pixel density.

It is desirable that the field lens in the present invention should be stationary with respect to the movable solid-state image pickup device. If the field lens is stationary, when focus control is effected by moving the solid-state image pickup device, the variation in the field angle can be minimized. Therefore, it is possible to obtain an image that gives no sense of incongruity to the observer, advantageously.

If a reflecting prism is placed immediately in front of the solid-state image pickup device, the diameter of the endoscope can be reduced favorably even when the size of the image pickup area is large. However, because of the angle dependence of the reflectance of the prism, if the variation in the incident angle is large, the brightness at the periphery of the image field reduces unfavorably. Stabilization of the incident angle of rays by use of a field lens is also effective in solving this problem.

Thus, according to the first aspect of the present invention, a field lens is arranged to act positively in a magnifying endoscope of the type in which a solid-state image pickup device is moved, thereby providing advantageous effects as well as effectively preventing color shading.

According to a second aspect of the present invention, the above-described image pickup optical system has a device for preventing entrance of unwanted light that is placed on the object side of the solid-state image pickup device.

Placing the unwanted light entrance preventing device on the object side of the solid-state image pickup device is effective from the viewpoint of flare prevention. As has already been stated above, the change of the ray height at the maximum field angle caused by the movement of the solid-state image pickup device is minimized by the action of the field lens in the arrangement according to the first aspect of the present invention. In this arrangement, if a flare stop is placed at a position where the change of the ray height is minimal, unwanted light can be cut off efficiently even if focus control is effected. It is desirable that the position where the change of the ray height is minimal should be in the vicinity of the field lens, more desirably immediately behind the field lens. When a reflecting prism is present between the field lens and the solid-state image pickup device, blocking extra-field light before it enters the reflecting prism is particularly effective in preventing the occurrence of flare.

According to a third aspect thereof, the present invention provides an optical system capable of being focused at a plurality of object distances by moving a solid-state image pickup device. The solid-state image pickup device includes at least an optically positioned optical element. The movement of the solid-state image pickup device is effected by sliding it using the outer peripheral portion of the optical element as reference.

Originally, the solid-state image pickup device has a large displacement between the center of the outer periphery thereof and the center of the effective area thereof. Therefore, to position the solid-state image pickup device accurately, it is preferable to cement a positioning optical element (e.g. a plane-parallel plate) to the front of the solid-state image pickup device and to slide the solid-state image pickup device by using the positioning optical element as a guide after making an adjustment such that the center of the outer periphery of the optical element is coincident with the center of the effective area of the solid-state image pickup device. By doing so, it is possible to prevent the center of the field from being displaced from the center axis of the endoscope even when the solid-state image pickup device is slid, without making the solid-state image pickup device costly.

Still other objects and advantages of the invention will in part be obvious and will in part be apparent from the specification.

The invention accordingly comprises the features of construction, combinations of elements, and arrangement of parts which will be exemplified in the construction hereinafter set forth, and the scope of the invention will be indicated in the claims.

DESCRIPTION OF THE PREFERRED EMBODIMENTS

Figure 3A:
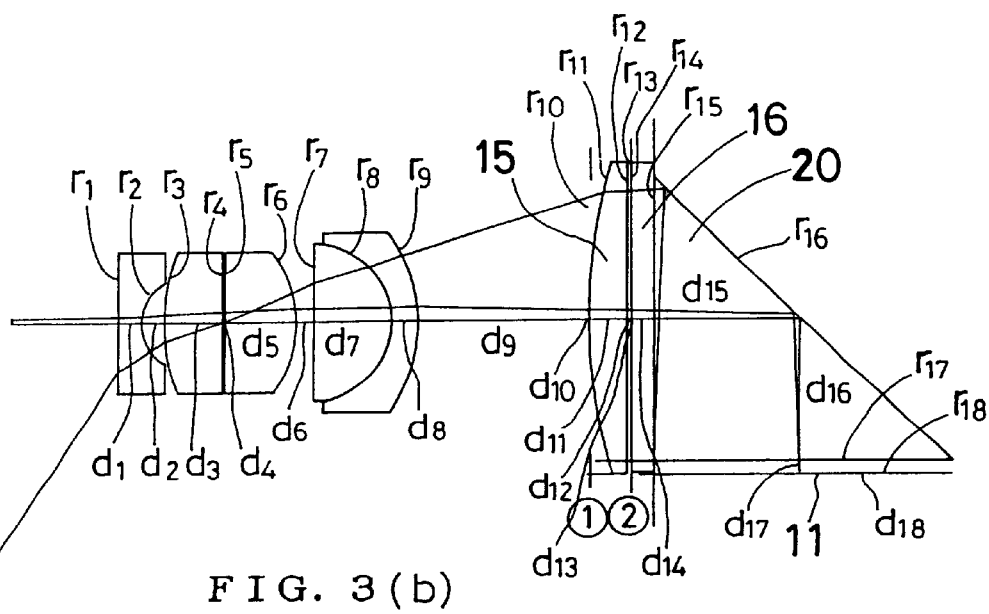
FIG. 3 is a sectional view of Example 2 of the magnifying endoscope optical system according to the present invention.
Figure 3B:
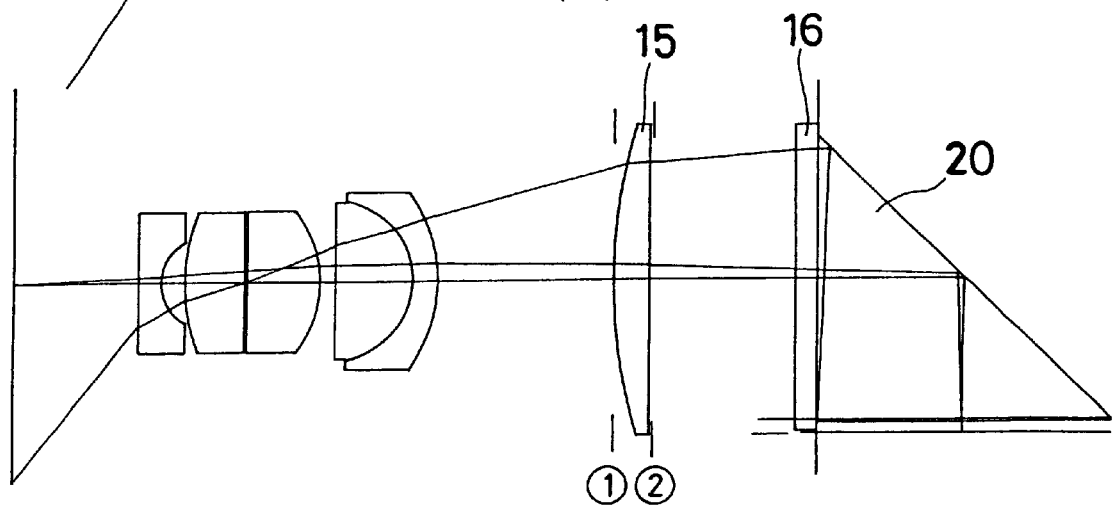
Figure 4A:
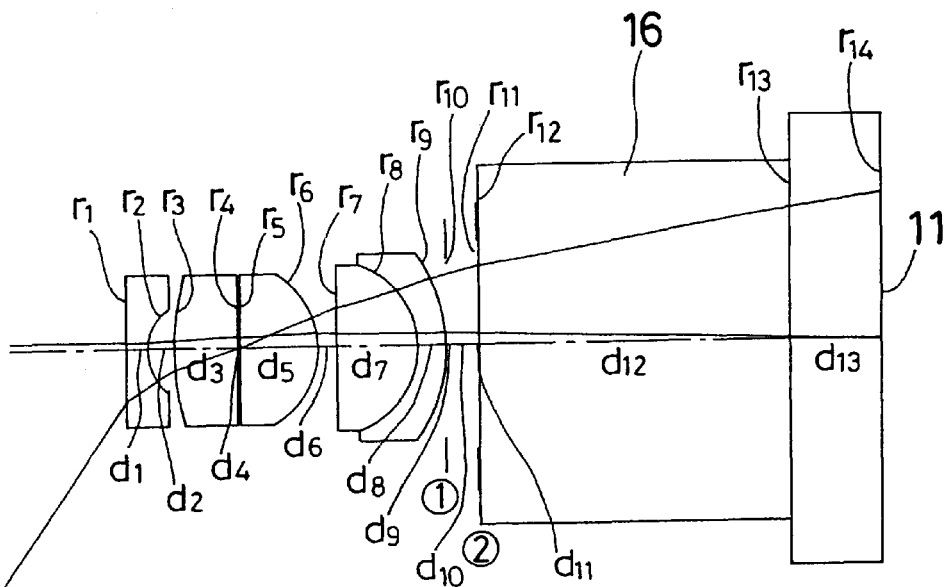
FIG. 4 is a sectional view of Example 3 of the magnifying endoscope optical system according to the present invention.
Figure 4B:
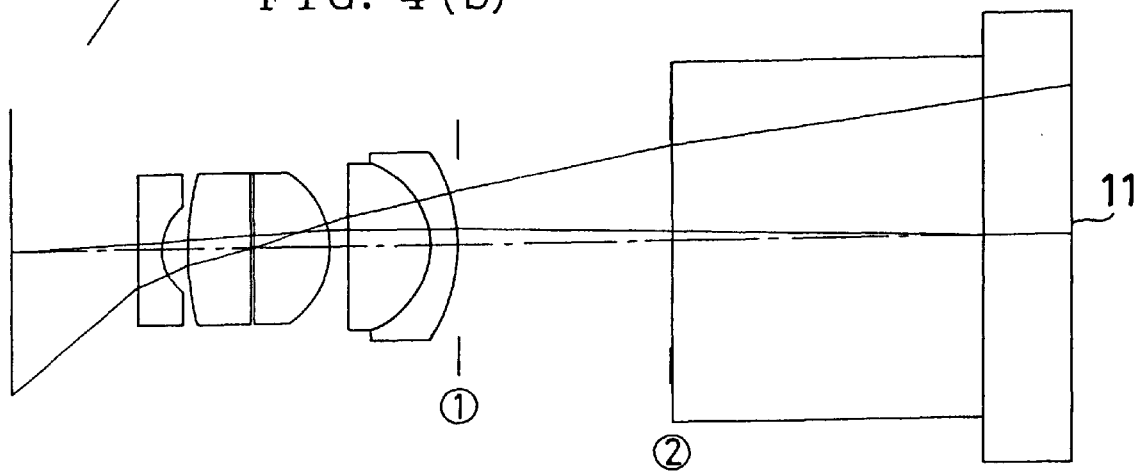

Examples 1 to 3 of the magnifying endoscope optical system according to the present invention will be described below with reference to FIGS. 2 to 4. In each of FIGS. 2 to 4, part (a) is a sectional view of the magnifying endoscope optical system when focused on a far object under observation, and part (b) is a sectional view of the magnifying endoscope optical system when focused on a near object under observation. Numerical data in these Examples will be shown later. In the tables showing the numerical data: $r_1, r_2 \ldots$ are the radii of curvature of lens surfaces; $d_1, d_2 \ldots$ are the spacings between adjacent lens surfaces; $n_{d1}, n_{d2} \ldots$ are the refractive indices of the lenses for the spectral d-line; and $v_{d1}, v_{d2} \ldots$ are the Abbe's numbers of the lenses. Further, $r_0$ denotes an object plane, and $d_0$ denotes an object distance.

Example 1

This is an example of the magnifying endoscope optical system according to the first, second and third aspects of the present invention. As shown in FIG. 2, the optical system according to this example has, in order from the object side, a plano-concave negative lens, a convexo-plane positive lens, a plano-convex positive lens, and a cemented lens consisting of a plano-convex positive lens and a negative meniscus lens having a convex surface directed toward the image side. A field lens 15 is fixedly placed on the image side of the cemented lens. The field lens 15 is a convexo-plane positive lens.

In this example, the field lens 15 is stationary with respect to a movable solid-state image pickup device 11. Therefore, it is possible to suppress the variation in the angle of incidence of light rays on the solid-state image pickup device 11 due to focus control. That is, when the optical system is focused on the far object [part (a) of FIG. 2], the incident angle is −3.982°. When the optical system is focused on the near object [part (b) of FIG. 2], the incident angle is −4.2610. It should be noted that when the far object is observed [part (a) of FIG. 2], the exit pupil position at the maximum image height is 14.36 millimeters toward the object from the image position. When the near object is observed [part (b) of FIG. 2], the exit pupil position is 13.41 millimeters toward the object from the image position. Therefore, color shading can be suppressed irrespective of focus control. The field lens 15 further has the effect of suppressing the variation in the field angle due to focus control. That is, when the optical system is focused on the far object, the field angle is 114.11°. When the optical system is focused on the near object, the field angle is 104.684°. Therefore, there is substantially no change in the field angle when the observation mode is changed to the close-up observation mode. Thus, it is possible to provide an image that gives no sense of incongruity to the user.

Further, in this example, the variation in the ray height at positions ① and ② near the field lens 15 is minimized by the action of the field lens 15. More specifically, when the optical system is focused on the far object, the ray height at the position ① is 0.941, and when the optical system is focused on the near object, the ray height aft the position ① is 0.892 (ray height difference: 0.049). The ray height at the position ② when the optical system is focused on the far object is 0.997, and the ray height at the position ② when the optical system is focused on the near object is 0.940 (ray height difference: 0.057). Thus, the ray height variation is small. Accordingly, if a flare stop is placed at the position ① or ②, a similar flare cut-off effect can be exhibited irrespective of focus control.

Let us evaluate the above-described advantageous effects in comparison to Example 3 (described later). Example 3 is an optical system in which a solid-state image pickup device is moved without using a field lens. Example 3 is an example of the optical system according to the third aspect of the present invention, to which the first and second aspects of the present invention are not applied.

In Example 3, the variation in the incident angle of light rays due to focus control is relatively large. That is, when the optical system is focused on the far object, the incident angle is −15.318°. When the optical system is focused on the near object, the incident angle is −11.751°. Accordingly, color shading occurs. In this case, when the far object is observed, the exit pupil position at the maximum image height is 3.65 millimeters toward the object from the image position. When the near object is observed, the exit pupil position is 4.81 millimeters toward the object from the image position. That is, it is possible to realize a state free from color shading by allowing the exit pupil position x (mm) to satisfy the condition of x>5 by the effect of the field lens in this example. In the sense of the angle at which rays are incident on the CCD, the condition for the exit pupil position may also be x<−5. In other words, |x|>5 (mm) is the condition for the exit pupil position.

In Example 3, the variation in the field angle due to focus control is unfavorably large. That is, when the optical system is focused on the far object, the field angle is 113.649°. When the optical system is focused on the near object, the field angle is 81.844°. Thus, the viewing range becomes unfavorably narrow when focus control is effected to observe the near object.

In Example 3, the variation in the ray height at positions ① and ② (FIG. 4) due to focus control is unfavorably large. More specifically, when the optical system is focused on the far object, the ray height at the position ① is 0.566, and when the optical system is focused on the near object, the ray height at the position ① is 0.458 (ray height difference: 0.108). The ray height at the position ② when the optical system is focused on the far object is 0.613, and the ray height at the position ② when the optical system is focused on the near object is 0.691 (ray height difference: 0.078). Accordingly, even if a flare stop is placed at the position ① or ②, some rays are undesirably left uncut off by the flare stop when focus control is effected, causing flare.

It will be clear from the comparison between Examples 1 and 3 that the use of a field lens in the optical systems according to the first and second aspects of the present invention is very effective.

Figure 1:
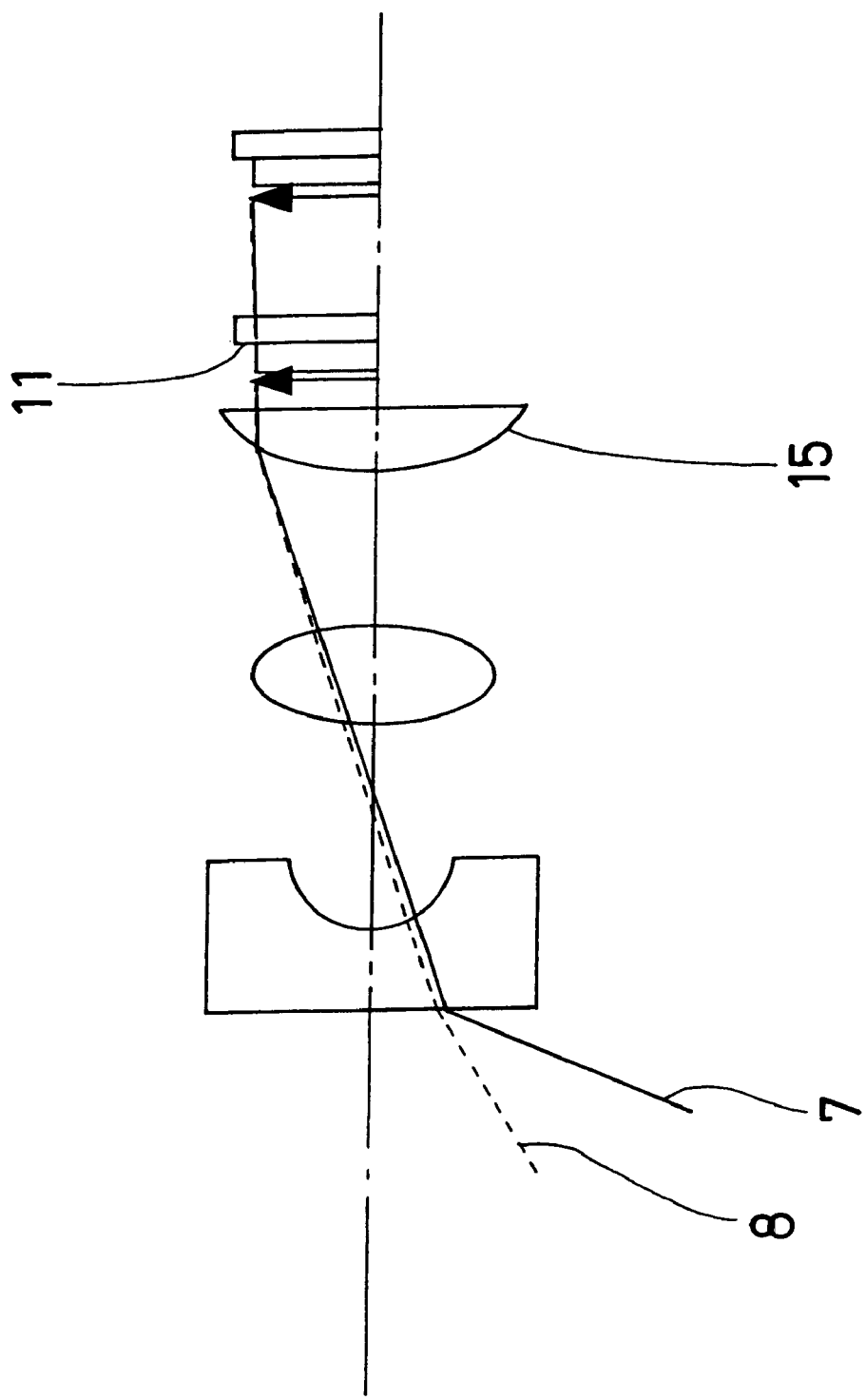
FIG. 1 is a conceptual view for describing the image pickup optical system according to the present invention.
Figure 2A:
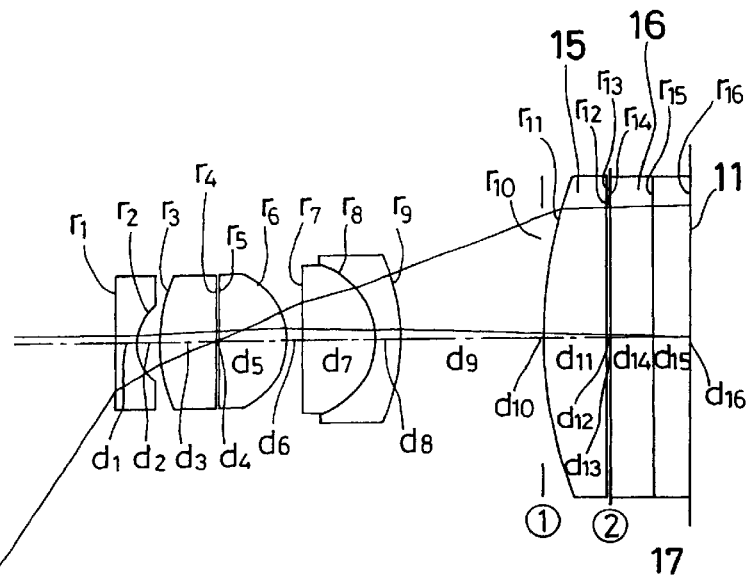
FIG. 2 is a sectional view of Example 1 of the magnifying endoscope optical system according to the present invention.
Figure 2B:
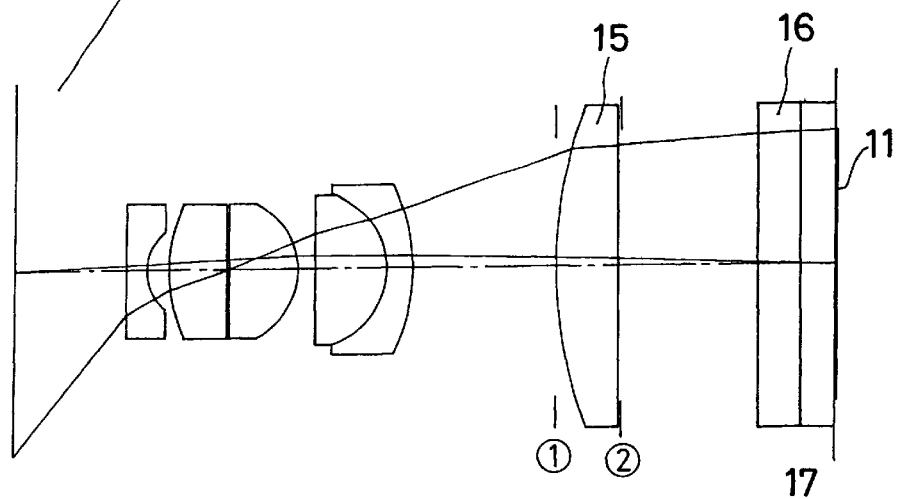
Figure 5A:
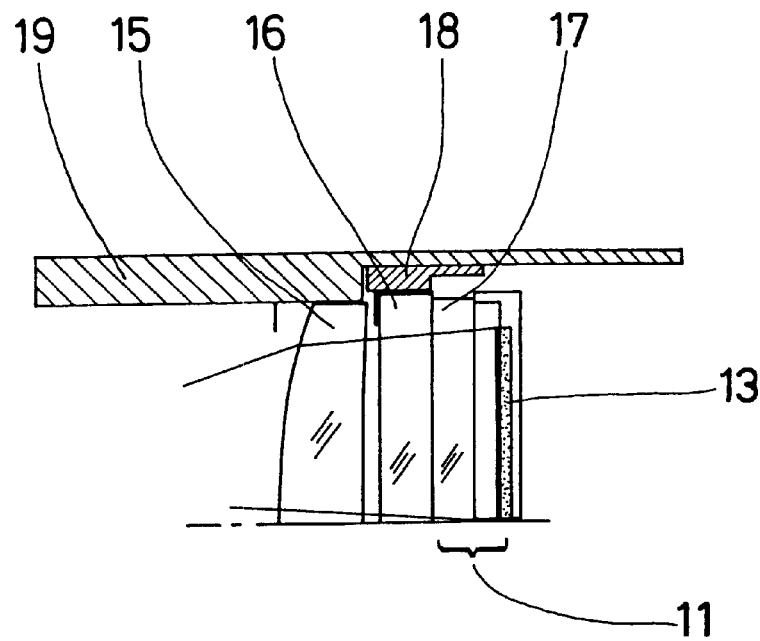
FIG. 5 is a sectional view showing the arrangement of Example 1, including a mechanism frame.
Figure 5B:
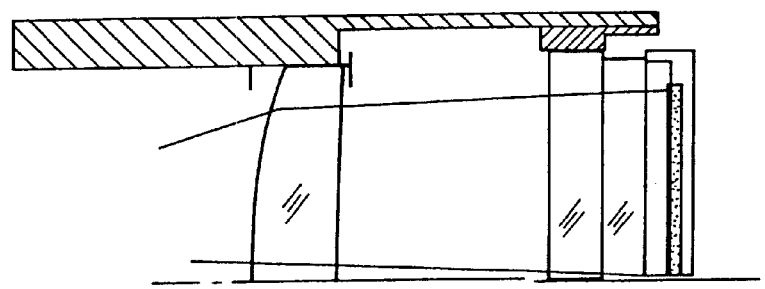

In this example, further, an optical element (plane-parallel plate) 16 shown in FIG. 2 is adjusted in advance so that the center of the optical element 16 and the center of the effective area of the solid-state image pickup device 11 are aligned with each other. Therefore, if a sliding surface is set by using the outer periphery of the optical element 16 as the reference, the center of the effective area of the solid-state image pickup device 11 is allowed to coincide with the optical axis of the optical system at all times. The arrangement of Example 1, including a mechanism frame, is shown in FIG. 5. In this example, the optical element 16 is cemented to the solid-state image pickup device 11 so that the center of the optical element 16 is aligned with the center of the effective area 13 of the solid-state image pickup device 11. Thus, even when the center of a cover glass 17 sealing the solid-state image pickup device 11 is not in alignment with the center of the effective area 13 of the solid-state image pickup device 11, the optical axis of the optical system and the center of the effective area 13 of the solid-state image pickup device 11 can be aligned with each other by using the outer periphery of the optical element 16 as the reference. In this example, the outer periphery of the optical element 16 is received with a mechanical member 18, and the mechanical member 18 is made to slide relative to a frame 19 that determines the optical axis of the optical system, thereby allowing the optical axis of the optical system and the center of the effective area 13 of the solid-state image pickup device 11 to be aligned with each other irrespective of the change in position [parts (a) and (b) of FIG. 5] due to focus control.

It should be noted that the flare stop only needs to be positioned with respect to the optical axis. Therefore, the flare stop may be positioned by using the frame 19 or the mechanical member 18 as the reference. Alternatively, the flare stop may be cemented to the field lens 15 or the optical element 16.

Example 2

This is an example of the magnifying endoscope optical system according to the first, second and third aspects of the present invention. As shown in FIG. 3, the optical system according to this example has, in order from the object side, a plano-concave negative lens, a convexo-plane positive lens, a plano-convex positive lens, and a cemented lens consisting of a plano-convex positive lens and a negative meniscus lens having a convex surface directed toward the image side. A field lens 15 is fixedly placed on the image side of the cemented lens. The field lens 15 is a convexo-plane positive lens. In addition, a movable solid-state image pickup device 11 is fixedly cemented to a rectangular prism 20. Focus control is effected by moving the solid-state image pickup device 11, together with the rectangular prism 20.

The variation in the incident angle of rays due to focus control is suppressed by the action of the fixed field lens 15. That is, when the optical system is focused on the far object, the incident angle is −4.080°. When the optical system is focused on the near object, the incident angle is −4.077°. It should be noted that when the far object is observed, the exit pupil position at the maximum image height is 14.1 millimeters toward the object from the image position. When the near object is observed, the exit pupil position is 14.1 millimeters toward the object from the image position. Therefore, color shading can be suppressed irrespective of focus control. The field lens 15 further has the effect of suppressing the variation in the field angle due to focus control. That is, when the optical system is focused on the far object, the field angle is 113.681°. When the optical system is focused on the near object, the field angle is 103.717°. Therefore, there is substantially no change in the field angle when the observation mode is changed to the close-up observation mode. Thus, it is possible to provide an image that gives no sense of incongruity to the user.

Although the rectangular prism 20 is used in this example, focus control can be effected without concern for the incident angle dependence of the reflectance of the reflecting surface because the field lens 15 is provided. Further, because the rectangular prism 20 is cemented to the solid-state image pickup device 11, it is possible to increase the distance from the solid-state image pickup device 11 to the entrance surface of the rectangular prism 20 and hence possible to enlarge the diameter of the light beam passing through the entrance surface. Accordingly, if dust is attached to the entrance surface of the rectangular prism 20, it is inconspicuous, advantageously.

Further, in this example, the variation in the ray height at positions ① and ② near the field lens 15 is minimized by the action of the field lens 15. More specifically, when the optical system is focused on the far object, the ray height at the position ① is 0.932, and when the optical system is focused on the near object, the ray height at the position ① is 0.881 (ray height difference: 0.051). The ray height at the position ② when the optical system is focused on the far object is 0.966, and the ray height at the position ② when the optical system is focused on the near object is 0.910 (ray height difference: 0.056). Thus, the ray height variation is small. Accordingly, if a flare stop is placed at the position ① or ②, the entrance of unwanted light can be prevented effectively. It should be noted that the flare stop may be symmetric with respect to the optical axis. It is also possible to reduce the size of the flare stop only in a direction in which a forceps channel is present, thereby enhancing the flare preventing effect. In this case, the flare stop has an irregular configuration with respect to the optical axis.

Figure 6A:
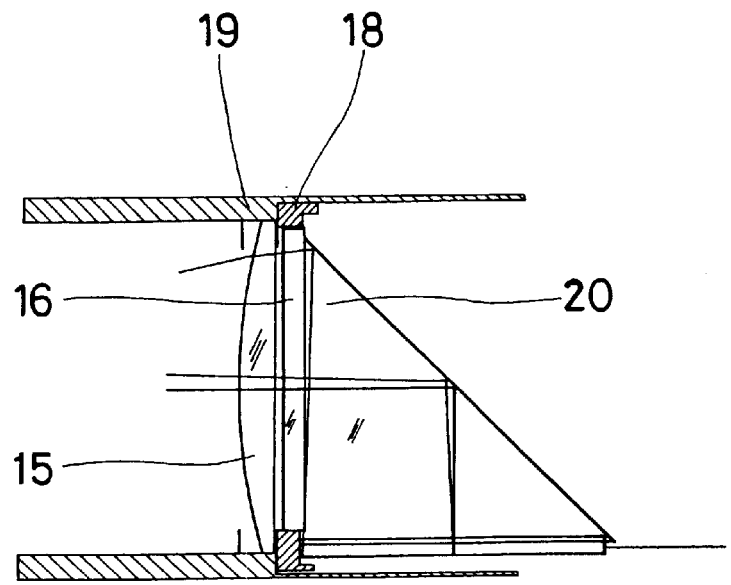
FIG. 6 is a sectional view showing the arrangement of Example 2, including a mechanism frame.
Figure 6B:
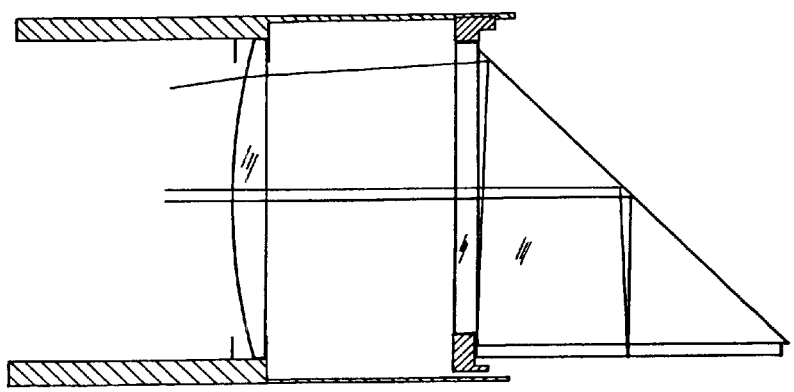

In this example, an optical element (plane-parallel plate) 16 is cemented to the rectangular prism 20 such that the center of the optical element 16 is aligned with the center of the effective area (not shown) of the solid-state image pickup device 11. Thus, the optical axis of the optical system and the center of the effective area of the solid-state image pickup device 11 can be aligned with each other by using the outer periphery of the optical element 16 as the reference. The arrangement of Example 2, including a mechanism frame, is shown in FIG. 6. In this example, the outer periphery of the optical element 16 is received with a mechanical member 18, and the mechanical member 18 is made to slide relative to a frame 19 that determines the optical axis of the optical system, thereby allowing the optical axis of the optical system and the center of the effective area of the solid-state image pickup device 11 to be aligned with each other irrespective of the change in position [parts (a) and (b) of FIG. 6] due to focus control. It is also possible to impart the effect of the optical element 16 to the field lens 15 by aligning the center of the outer periphery of the field lens 15 with the center of the effective area of the solid-state image pickup device 11 from the viewpoint of the frame structure.

The flare stop only needs to be positioned with respect to the optical axis. Therefore, the flare stop may be positioned by using the frame 19 or the mechanical member 18 as the reference. Alternatively, the flare stop may be cemented to the field lens 15, the optical element 16 or the prism 20.

Example 3

This is an example of the magnifying endoscope optical system according to the third aspect of the present invention, although a field lens is not used in this example. As shown in FIG. 4, the optical system according to this example has, in order from the object side, a plano-concave negative lens, a convexo-plane positive lens, a plano-convex positive lens, and a cemented lens consisting of a plano-convex positive lens and a negative meniscus lens having a convex surface directed toward the image side.

Figure 7A:
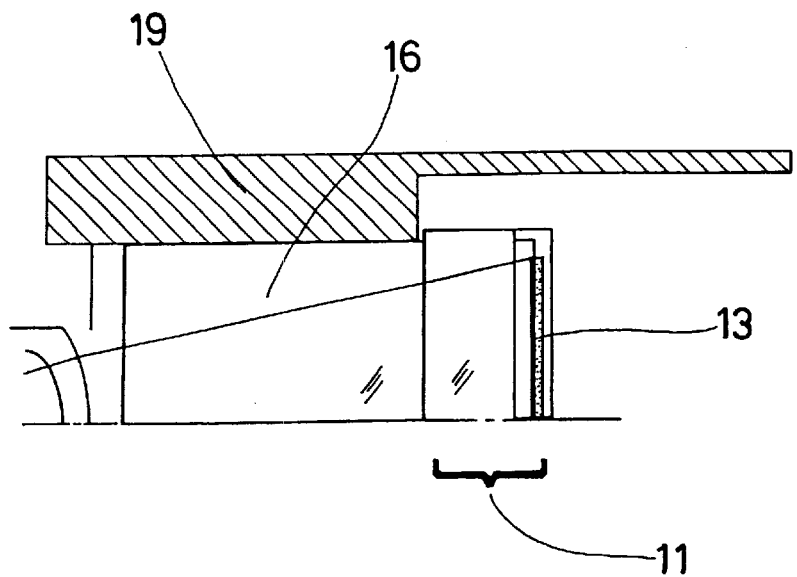
FIG. 7 is a sectional view showing the arrangement of Example 3, including a mechanism frame.
Figure 7B:
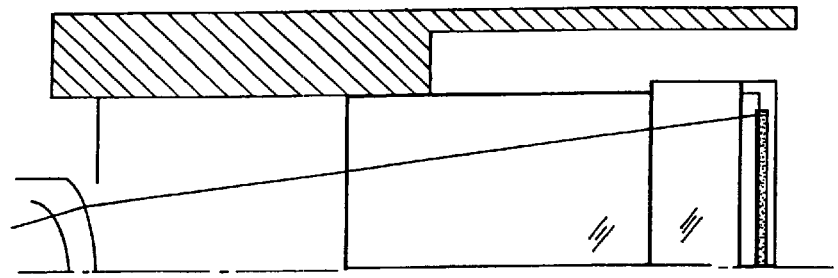
Figure 8:
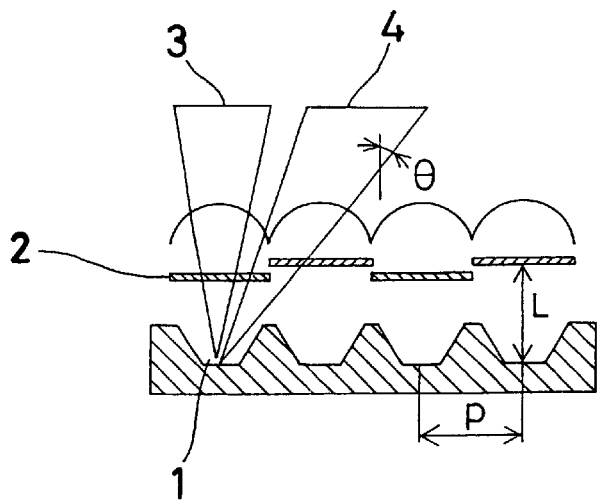
FIG. 8 is a conceptual view of the cross-section of a simultaneous solid-state image pickup device.
Figure 9:
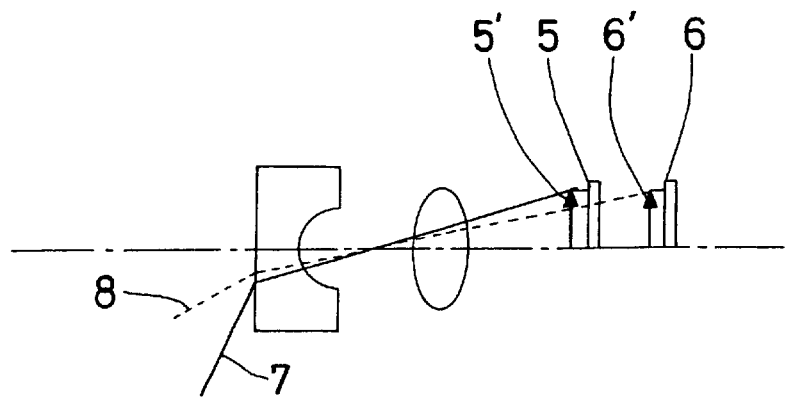
FIG. 9 is a conceptual view showing an image position and a solid-state image pickup device position when a conventional optical system is focused on a far object and also showing an image position and a solid-state image pickup device position when the optical system is focused on a near object.
Figure 10:
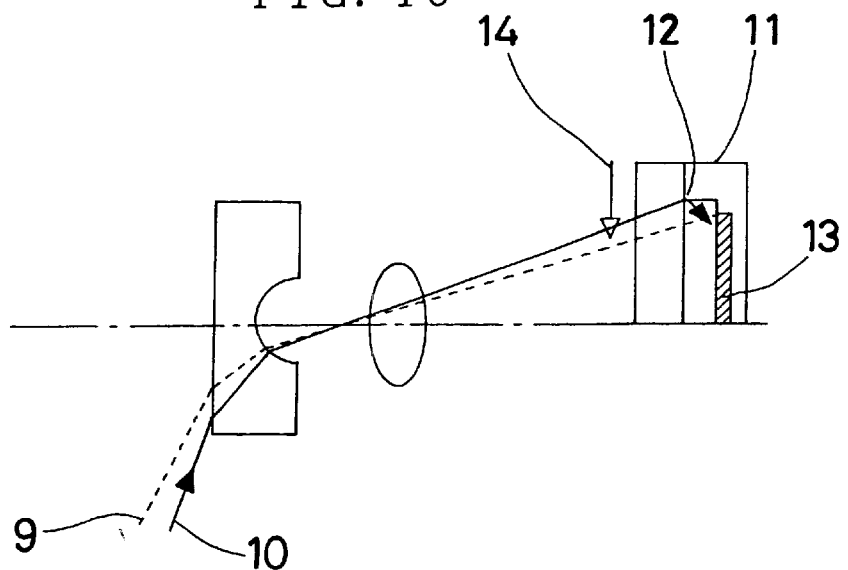
FIG. 10 is a diagram showing a light ray at the maximum field angle in a wide-angle optical system, together with light outside the field.

In this example, an optical element (plane-parallel plate) 16 is cemented to a cover glass 17 of a solid-state image pickup device 11 such that the center of the optical element 16 is aligned with the center of the effective area (not shown) of the solid-state image pickup device 11. Thus, the optical axis of the optical system and the center of the effective area of the solid-state image pickup device 11 can be aligned with each other by using the outer periphery of the optical element 16 as the reference. The arrangement of Example 3, including a mechanism frame, is shown in FIG. 7. In this example, the outer periphery of the optical element 16 is made to slide relative to a frame 19 that determines the optical axis of the optical system, thereby allowing the optical axis of the optical system and the center of the effective area 13 of the solid-state image pickup device 11 to be aligned with each other irrespective of the change in position [parts (a) and (b) of FIG. 7] due to focus control.

Numerical data concerning the optical systems according to the above-described Examples 1 to 3 is shown below.

Example 1

| | | | |
|---|---|---|---|
| $r_0 = \infty$ (Object) | $d_0$ = (Variable) | | |
| $r_1 = \infty$ | $d_1 = 0.1534$ | $n_{d1} = 1.57135$ | $v_{d1} = 52.95$ |
| $r_2 = 0.3693$ | $d_2 = 0.1678$ | | |
| $r_3 = 1.3513$ | $d_3 = 0.4111$ | $n_{d2} = 1.80518$ | $v_{d2} = 25.42$ |
| $r_4 = \infty$ | $d_4 = 0.0163$ | | |
| $r_5 = \infty$ | $d_5 = 0.5081$ | $n_{d3} = 1.48749$ | $v_{d3} = 70.23$ |
| $r_6 = -0.5552$ | $d_6 = 0.1217$ | | |
| $r_7 = \infty$ | $d_7 = 0.5332$ | $n_{d4} = 1.53996$ | $v_{d4} = 59.46$ |
| $r_8 = -0.5801$ | $d_8 = 0.1775$ | $n_{d5} = 1.80518$ | $v_{d5} = 25.42$ |
| $r_9 = -1.4980$ | $d_9 = 1.0311$ | | |
| $r_{10} = \infty$ (①) | $d_{10} = 0.0000$ | | |
| $r_{11} = 3.3494$ | $d_{11} = 0.4558$ | $n_{d6} = 1.88300$ | $v_{d6} = 40.76$ |
| $r_{12} = \infty$ | $d_{12} = 0.0200$ | | |
| $r_{13} = \infty$ (②) | $d_{13}$ = (Variable) | | |
| $r_{14} = \infty$ | $d_{14} = 0.3000$ | $n_{d7} = 1.51633$ | $v_{d7} = 64.14$ |
| $r_{15} = \infty$ | $d_{15} = 0.2500$ | $n_{d8} = 1.51633$ | $v_{d8} = 64.14$ |
| $r_{16} = \infty$ | $d_{16} = 0.0021$ | | |
| $r_{17} = \infty$ (Image plane) | | | |

| Variable data | | |
|---|---|---|
| $d_0$ | 13.0000 | 0.8140 |
| $d_{13}$ | 0.0057 | 0.9768 |

Example 2

| | | | |
|---|---|---|---|
| $r_0 = \infty$ (Object) | $d_0$ = (Variable) | | |
| $r_1 = \infty$ | $d_1 = 0.1534$ | $n_{d1} = 1.57135$ | $v_{d1} = 52.95$ |
| $r_2 = 0.3133$ | $d_2 = 0.1678$ | | |
| $r_3 = 1.4897$ | $d_3 = 0.4111$ | $n_{d2} = 1.80518$ | $v_{d2} = 25.42$ |
| $r_4 = \infty$ | $d_4 = 0.0163$ | | |
| $r_5 = \infty$ | $d_5 = 0.5081$ | $n_{d3} = 1.48749$ | $v_{d3} = 70.23$ |
| $r_6 = -0.8347$ | $d_6 = 0.1217$ | | |
| $r_7 = \infty$ | $d_7 = 0.5332$ | $r_{d4} = 1.53996$ | $v_{d4} = 59.46$ |
| $r_8 = -0.5656$ | $d_8 = 0.1775$ | $n_{d5} = 1.80518$ | $v_{d5} = 25.42$ |
| $r_9 = -1.0796$ | $d_9 = 1.2099$ | | |
| $r_{10} = \infty$ (①) | $d_{10} = 0.0000$ | | |
| $r_{11} = 3.9810$ | $d_{11} = 0.2500$ | $n_{d6} = 1.88300$ | $v_{d6} = 40.76$ |
| $r_{12} = \infty$ | $d_{12} = 0.0200$ | | |
| $r_{13} = \infty$ (②) | $d_{13}$ = (Variable) | | |
| $r_{14} = \infty$ | $d_{14} = 0.1500$ | $n_{d7} = 1.51633$ | $v_{d7} = 64.14$ |
| $r_{15} = \infty$ | $d_{15} = 1.0000$ | $n_{d8} = 1.51633$ | $v_{d8} = 64.14$ |
| $r_{16} = \infty$ | $d_{16} = -1.0000$ | $n_{d9} = 1.51633$ | $v_{d9} = 64.14$ |
| $r_{17} = \infty$ | $d_{17} = -0.1000$ | $n_{d10} = 1.51633$ | $v_{d10} = 64.14$ |
| $r_{18} = \infty$ | $d_{18} = 0.0844$ | | |
| $r_{19} = \infty$ (Image plane) | | | |

| Variable data | | |
|---|---|---|
| $d_0$ | 7.3260 | 0.8600 |
| $d_{13}$ | 0.0057 | 0.9768 |

Example 3

| | | | |
|---|---|---|---|
| $r_0 = \infty$ (Object) | $d_0$ = (Variable) | | |
| $r_1 = \infty$ | $d_1 = 0.1534$ | $n_{d1} = 1.57135$ | $v_{d1} = 52.95$ |
| $r_2 = 0.3578$ | $d_2 = 0.1678$ | | |
| $r_3 = 1.8555$ | $d_3 = 0.4111$ | $n_{d2} = 1.80518$ | $v_{d2} = 25.42$ |
| $r_4 = \infty$ | $d_4 = 0.0163$ | | |
| $r_5 = \infty$ | $d_5 = 0.5081$ | $n_{d3} = 1.48749$ | $v_{d3} = 70.23$ |
| $r_6 = -0.5889$ | $d_6 = 0.1217$ | | |
| $r_7 = \infty$ | $d_7 = 0.5332$ | $n_{d4} = 1.53996$ | $v_{d4} = 59.46$ |
| $r_8 = -0.5918$ | $d_8 = 0.1775$ | $n_{d5} = 1.80518$ | $v_{d5} = 25.42$ |
| $r_9 = -1.1384$ | $d_9 = 0.0000$ | | |
| $r_{10} = \infty$ (①) | $d_{10}$ = (Variable) | | |
| $r_{11} = \infty$ (②) | $d_{11} = 0.0100$ | | |
| $r_{12} = \infty$ | $d_{12} = 2.0000$ | $n_{d6} = 1.51633$ | $v_{d6} = 64.14$ |
| $r_{13} = \infty$ | $d_{13} = 0.5672$ | $n_{d7} = 1.51633$ | $v_{d7} = 64.14$ |
| $r_{14} = \infty$ | $d_{14} = 0.0000$ | | |
| $r_{15} = \infty$ (Image plane) | | | |

| Variable data | | |
|---|---|---|
| $d_0$ | 7.3260 | 0.8140 |
| $d_{10}$ | 0.2031 | 1.3757 |

The specifications of the above-described Examples 1 to 3 are as follows.

| | | Ex. 1 | Ex. 2 | Ex. 3 |
|---|---|---|---|---|
| Focal length | | 1.038 | 1.099 | 1.056 |
| Image height | | 1 | 1 | 1 |
| F-number | Far observation | 9.631 | 11.119 | 10.558 |
| CCD incident | Far observation | −3.982 | −4.080 | −15.318 |
| angle (°) | Near observation | −4.261 | −4.077 | −11.751 |
| Field angle | Far observation | 114.110 | 113.681 | 113.649 |
| (°) | Near observation | 104.684 | 103.717 | 81.844 |
| Ray height at flare | Far observation | 0.941 | 0.932 | 0.566 |
| stop position ① | Near observation | 0.892 | 0.881 | 0.458 |
| Ray height at flare | Far observation | 0.997 | 0.966 | 0.613 |
| stop position ② | Near observation | 0.940 | 0.910 | 0.691 |
| Exit pupil | Far observation | −14.36 | −14.1 | −3.65 |
| position | Near observation | −13.41 | −14.1 | −4.81 |

Thus, in the image pickup optical system according to the present invention, a field lens is combined with an optical system arrangement in which a solid-state image pickup device is moved, thereby realizing an optical system capable of satisfactorily suppressing color shading when a simultaneous solid-state image pickup device is used.

In addition, it is possible to realize an optical system in which flare is satisfactorily suppressed even when focus control is effected by appropriately positioning a flare stop in the optical system.

In addition, it is possible to realize an optical system reduced in cost as a whole even if it uses a solid-state image pickup device having a large displacement between the center of the outer periphery thereof and the center of the effective area thereof by devising a scheme to position the effective area of the solid-state image pickup device so that the displacement between the center of the field and the center axis of the endoscope caused by focus control gives rise to no problem.

The feasibility of the magnifying endoscope in which a solid-state image pickup device is moved is further enhanced by devising the above-described schemes.

What we claim is:

1. An endoscope system having an image pickup optical system capable of being focused at a plurality of object distances to allow an enlarged image to be observed, said endoscope system comprising:

an image-forming optical system for forming an object image; and a solid-state image pickup device for converting the image formed by said image-forming optical system into an electric signal;

wherein when focus control is effected by moving said solid-state image pickup device in a direction of an optical axis, principal rays emerging from said image-forming optical system are telecentric so as to be incident approximately perpendicularly on a light-receiving surface of said solid-state image pickup device at all times irrespective of a state of movement of said solid-state image pickup device for focus control.

2. An endoscope system according to claim 2, further comprising:

a field lens for maintaining telecentricity, said field lens being formed from at least one positive lens, said field lens being provided between said image-forming optical system and said solid-state image pickup device.

3. An endoscope system according to claim 2, wherein said field lens is fixed with respect to said image-forming optical system, so that said field lens does not move when said solid-state image pickup device moves.

4. An endoscope system according to claim 1, 2 or 3, wherein said solid-state image pickup device is a simultaneous solid-state image pickup device, wherein when said solid-state image pickup device has a color filter corresponding to each pixel, the following condition is satisfied:

$$\theta < \tan^{-1}(p/2L)$$

where $\theta$ is a maximum incident angle of rays, inclusive of an angle subtended by rays that depend on an F-number; p is a pixel pitch; and L is a distance to a farthest color filter from a light-receiving part.

5. An endoscope system according to claim 4, wherein said solid-state image pickup device has at least 800,00 pixels.

6. An endoscope system according to claim 1, 2, of 3, wherein said solid-state image pickup device has at least 800,000 pixels.

7. An endoscope system according to claim 2, further comprising:

entrance preventing means for preventing entrance of unwanted light, said entrance preventing means being provided in a vicinity of said field lens either in front of or behind said field lens.

8. An endoscope system according to claim 7, wherein said entrance preventing means is provided on a side of said field lens closer to said solid-state image pickup device.

9. An endoscope system according to claim 7, wherein when a reflecting prism is placed immediately in front of said solid-state image pickup device, said entrance preventing means is provided between said field lens and said reflecting prism.

10. An endoscope system having an image pickup optical system capable of being focused at a plurality of object distances to allow an enlarged image to be observed, said endoscope system comprising:

an image-forming optical system for forming an object image; and a solid-state image pickup device for converting the image formed by said image-forming optical system into an electric signal;

wherein when focus control is effected by moving said solid-state image pickup device in a direction of an optical axis, said solid-state image pickup device has a centering optical element integrated therewith so that a center of effective pixels and an optical axis of the optical system will not be displaced from each other as said solid-state image pickup device is moved, and wherein said solid-state image pickup device is moved in the direction of the optical axis by using an outer peripheral portion of said centering optical element as a reference.

11. An endoscope system according to claim 10, wherein said centering optical element is a plane-parallel plate.

* * * * *